United States Patent [19]

Scolastico et al.

[11] 4,440,688
[45] Apr. 3, 1984

[54] NOVEL DERIVATIVES OF URSODEOXYCHOLIC ACID

[76] Inventors: Carlo Scolastico, Vallisneri Street 13B; Cesare Sirtori, Bossi Street 1, both of Milan, Italy; David Kritchevsky, 36 St. at Spruce, Philadelphia, Pa. 19105

[21] Appl. No.: 392,634

[22] Filed: Jun. 28, 1982

[30] Foreign Application Priority Data

Jul. 24, 1981 [IT] Italy .............................. 23108 A/81

[51] Int. Cl.³ .............................................. C07J 13/00
[52] U.S. Cl. .................................................. 260/397.1
[58] Field of Search ..................................... 260/397.1

[56] References Cited

U.S. PATENT DOCUMENTS 3,833,620  9/1974  Saltzman ........................ 260/397.1
4,282,161  8/1981  Guillemette et al. ............ 260/397.1

*Primary Examiner*—Elbert L. Roberts
*Attorney, Agent, or Firm*—Bucknam and Archer

[57] ABSTRACT

Novel compounds which are 7-acylderivatives of ursodeoxycholic acid are described of formula

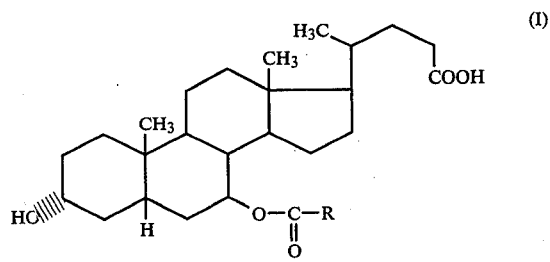

in which R-CO is the residue from a linear, saturated or unsaturated, carboxylic acid of 2–18 carbon atoms or the residue from a cycloalkanecarboxylic acid of 3–7 carbon atoms in the cycloalkane ring. The novel compounds are useful in the therapy of biliary calculosis, biliary diskinesia and hypertriglyceridemia.

1 Claim, No Drawings

NOVEL DERIVATIVES OF URSODEOXYCHOLIC ACID

The present invention relates to novel derivatives of ursodeoxycholic acid and more specifically to 7-acyl derivatives of ursodeoxycholic acid of formula I:

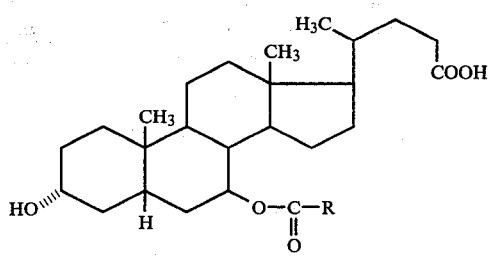

in which R—CO is the residue of a linear, saturated or unsaturated carboxylic acid having 2–18 carbon atoms or the residue of a cycloalkane carboxylic acid having 3–7 carbon atoms in the cycloalkane ring.

In particular, R—CO may be the acyl residue from acetic acid, butyric acid, caprylic acid, lauric acid, palmitic acid, stearic acid, oleic acid, linoleic acid, arachidonic acid, cyclopropanecarboxylic acid, cyclobutanecarboxylic acid, cyclopentanecarboxylic acid, and cyclohexanecarboxylic acid.

The therapy of biliary calculosis with ursodeoxycholic acid today is well-established, (Nakagawa and Makino, Lancet 2, 367, 1977). Ursodeoxycholic acid has been shown to be more effective than its epimer in the 7 position, that is chenodeoxycholic acid, particularly because of its lower susceptibility to inactivation of the hydroxy group in the 7-position. Enzymes of bacterial origin present at the intestinal level, (Ferrari, et al., FEBS Lett. 75, 176, 1977), are capable of removing the hydroxyl group in the 7α-position in chenodeoxycholic acid which is formed by the epimerization of ursodeoxycholic acid. For this reason, that is the slower inactivation with respect to chenodeoxycholic acid, ursodeoxycholic acid may be administered in lower dosages and is better tolerated. Further, on the basis of comparative studies, its clinical antilithiasis activity appears to be relatively inferior to that of chenodeoxycholic acid, (Nakayama, Digestive Dis. Sc. 25, 129, 1980). A metabolic inactivation in men of ursodeoxycholic acid has been described, presumably involving oxidation to a 7-ketoderivative, which makes the substance inactive during the course of 24 hours, (Fedorowski, et al, Gastroenterology 73, 1131, 1977).

The possibility that ursodeoxycholic acid may be, during a longer period of time, dehydroxylated in the 7-position, may involve the formation of metabolites of hepatoxic activity, (Sarva, et al, Gastroenterology, 79, 1980) and even mutagens in the intestine, (Sauer, et al., Zschr. Gastroenterol. 17, 236, 1979).

It is, therefore, very important for the purpose of achieving long-lasting therapy of biliary calculosis to provide derivatives which permit a continuous recycling of ursodeoxycholic acid and which reduce the possibility of inactivation at the intestinal level.

It has now been found that the 7-acylderivatives of formula I, which will be referred to hereinbelow with the symbol UDC-7-esters, resist this inactivation to an extent, which was unforeseeable, permitting a significant reduction in the daily doses and/or a significant increase in the intervals of administration. The acylderivatives of formula I result to be essentially devoid of toxicity in animals and in the course of experiments on experimental calculosis, have shown an antilithiasis activity, which particularly in certain respects, is substantially superior to the activity of ursodeoxycholic acid.

It is an object of the present invention to provide pharmaceutical compositions for the thereapy of biliary calculosis and diskinesia, which compositions comprise one or more UDC-7-esters as the active ingredient.

A further object of the invention resides in the use of the compounds of formula I for the therapy of biliary calculosis and biliary diskinesia.

The term "use" within the scope of the present invention, means all the operations inherent in the preparation of the compounds, including their purification, their formulation in pharmaceutical forms, suitable for the administration and/or the packaging in containers suitable for the administration itself.

Still another object of the present invention is to provide a process for the preparation of the compounds UDC-7-esters of formula I, which consists if the selective hydrolysis under alkaline conditions of 3,7-diacylderivatives of the methyl ester of ursodeoxycholic acid of formula II in accordance with the reaction scheme hereinbelow

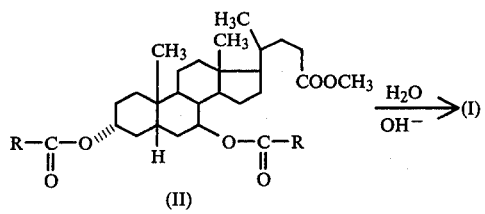

in which R—CO has the meaning indicated hereinabove.

The selective hydrolysis as illsutrated above is carried out with sodium hydroxide or potassium hydroxide in solvents, which consists of mixtures of lower alcohols with water or methyl cellosolve with water or analogous mixtures. The starting materials, that is the 3,7-diacylderivative of formula (II) are prepared by acylation of the methyl ester of ursodeoxycholic acid with active derivatives of the acids of formula R—COOH, such as the chlorides and the anhydrides, including mixed anhydrides, advantageously in the presence of an acid acceptor. A particularly simple method of diacylation, which is accompanied by good yields, consists of reacting the methyl ester of ursodeoxycholic acid and the acyl chloride or anhydride in pyridine.

After the selective hydrolysis illustrated hereinabove, the UDC-7-esters of formula (I) are isolated and purified by crystallization or if they are liquid at room temperature by chromatography on a column, suitably over silica. The examples hereinbelow illustrated the process according to the present invention.

EXAMPLE 1

7-butyryl-ursodeoxycholic acid, (formula I in which R=normal propyl)

(a) a solution of 1 millimole of the methyl ester of ursodeoxycholic acid in 1.42 cc of pyridine is treated with 9.8 millimoles of butyric anhydride. The mixture is warmed under reflux for three hours, then it is poured under stirring into ice and is acidified to pH of 1 with 1:1 HCl. The precipitate is extracted with CH$_2$Cl$_2$; the organic solvent is washed with a saturated solution of sodium bicarbonate then with water up to neutrality. The solution is dried over Na$_2$SO$_4$ and is then evaporated under vacuum up to constant weight. The product thus obtained, consisting of the methyl ester of 3,7-dibutyrylursodeoxycholic acid, is used without further purification for the subsequent reaction.

(b) a solution of 1 millimole of the diacylderivative obtained according to (a) above, in 4.46 cc of methanol is added to 2.23 cc of water and 0.23 cc of KOH in a 50% aqueous solution. The mixture is allowed to stand at room temperature in an inert atmosphere up to the point when chromatographic examination confirms that hydrolysis has occured, (about 2.5 hours); methanol is then evaporated under vacuum, the residue is acidified to a pH of 2 with 1:1 HCl and is then extracted with methylene chloride. The extract is dried over Na$_2$SO$_4$ and is then evaporated to dryness. After recrystallization from ethyl acetate, the desired product is obtained in pure state. m.p. 184°–185° C. (The analytical data are shown in Table 1).

EXAMPLE 2

7-oleyl-ursodeoxycholic acid (formula I, with R=CH$_3$—(CH$_2$)$_7$—CH=CH—(CH$_2$)$_7$—).

(a) a solution of 1 millimole of the methyl ester of ursodeoxycholic acid in 2 cc of pyridine is treated with 2.5 millimole of oleic acid chloride. The mixture is warmed under relfux for one hour then it is poured into ice, acidified with 1:1 HCl to pH of 1. The product, the methylester of 3,7-dioleylursodeoxycholic acid is isolated in the same manner as in Example 1a).

(b) the crude product obtained as described hereinabove is treated with KOH in aqueous methanol in the same quantitative proportions as indicated in example 1b, however, the hydrolysis is carried out under stirring at 50°–60° C. The oil obtained at the end of the operation is chromatographed over silica in the ratio 1:20 using as the eluent, mixtures of hexane/ethyl acetate in a ratio of increasing polarity from 9:1 to 6:4.

Table 1 hereinbelow summarizes the characteristic data of UDC-7-esters of formula (I) obtained according to the process of the present invention.

TABLE 1

| COMPOUND | m.p. °C. | Solvent of Crystallization | Formula | Analysis Calcd. % | Found % |
|---|---|---|---|---|---|
| UDC-7-acetate | — | — | C$_{26}$H$_{42}$O$_5$ C | 71.89 | 71.42 |
|  |  |  | H | 9.68 | 10.15 |
| UDC-7-butyrate | 184–185° C. | ethyl acetate | C$_{28}$H$_{46}$O$_5$ C | 72.73 | 72.52 |
|  |  |  | H | 9.96 | 10.19 |
| UDC-7-cyclopropancarboxylate | 214–216° C. | methanol | C$_{28}$H$_{44}$O$_5$ C | 73.04 | 72.74 |
|  |  |  | H | 9.57 | 9.87 |
| UDC-7-caprylate | oil | — | C$_{32}$H$_{54}$O$_5$ C | 74.13 | 74.00 |
|  |  |  | H | 10.42 | 10.79 |
| UDC-7-laurate | oil | — | C$_{36}$H$_{62}$O$_5$ C | 75.26 | 74.70 |
|  |  |  | H | 10.80 | 11.12 |
| UDC-7-oleate | oil | — | C$_{42}$H$_{72}$O$_5$ C | 76.83 | 77.08 |
|  |  |  | H | 10.98 | 11.01 |
| UDC-7-linoleate | oil | — | C$_{42}$H$_{70}$O$_5$ C | 77.06 | 77.12 |
|  |  |  | H | 10.70 | 10.83 |

The UDC-7-esters reported hereinabove give the following signals on NMR analysis (in pyridine with internal reference, TMS) and the following signals:
3.55/3.60–4.05/4.15 (1 H, m, >CHOH);
4.75/4.80–5.25/5.30 (1 H, m, >CH—O—OC—R);

The oleate and the linoleate in addition exhibit the signals at 5.27–5.60 (2H, m, CH=CH) and at 5.05–5.75, (4H, 2 CH=CH) respectively.

On infrared analysis, all the compounds of formula (I) exhibit an absorption at 3540 and 3420 cm$^{-1}$, (OH), and at 1720 cm$^{-1}$ (enlarged band: COOH, O—OC—R).

In order to evaluate the antilithiasis activity of ursodeoxycholic acid and its derivatives of formula (I), these substances have been tested on a model animal of calculosis. The test has been carried out by inducing calculosis caused by diet, which causes lithiasis, (Dam and Christensen, Acta Path. Microbiol. Scand. 30, 236, 1952), administered for a period of 53 days to Syrian Cricetidae. Ursodeoxycholic acid and its derivatives of formula (I) have been administered in doses equivalent to 0.2% of ursodeoxycholic acid. At the end of the treatment, the animals have been sacrificed and the appearance of the bile has been classified as clear or opaque and the percentage incidence of calculosis has been noted. The experimental data are reported in Table 2.

TABLE 2

Incidence of Calculosis in Cricetidae Treated with a Lithogenic Diet (group of 25 animals treated for a period of 53 days)

| | % of diet | Clear Bile | Opaque Bile | Calculi |
|---|---|---|---|---|
| Controls | — | 10/25 (40%) | 5/25 (20%) | 10/25 (40%) |
| Ursodeoxycholic acid (UDC) | 0.2 | 8/24 (33%) | 12/24 (50%) | 4/24 (17%) |
| UDC-acetate | 0.214 | 12/22 (44%) | 6/22 (27%) | 4/22 (18%) |
| UDC-laurate | 0.293 | 8/25 (32%) | 11/25 (44%) | 6/25 (24%) |
| UDC-butyrate | 0.236 | 4/24 (17%) | 12/24 (50%) | 9/24 (38%) |
| UDC-oleate | 0.335 | 18/25 (72%) | 7/25 (28%) | 0/25 (0%) |
| UDC-linoleate | 0.336 | 14/25 (53%) | 11/25 (44%) | 0/25 (0%) |

The animals treated with ursodeoxycholic acid or its 7-acylderivatives have not manifested toxic effects of significance and the lower mortality, 10% at the most per group, has been caused by episodes of infection, which are frequent in this type of experiment. The data show that ursodeoxycholic acid is an effective agent to prevent biliary calculosis, induced by lithogenic diet. On the other hand, the 7-acylderivatives of ursodeoxycholic acid, both the substances with a short chain substituent, as well as the substances with a long chain substituent, result equally or more active; in particular the derivatives with an unsaturated long chain substituent, show the ability to protect totally the animals against the incidence of calculosis.

The toxicity of ursodeoxycholic acid and its 7-acyl-derivatives has been tested in Swiss male rats and Swiss female rats of weight between 30 and 35 grams in the case of the male rats and 24-29 grams in the case of the female rats. Ursodeoxycholic acid and its 7-acylderivatives have been administered, dissolved in 0.5% carboxymethyl cellulose. Increasing doses from 10 mg per kg up to 2,000 mg per kg for each substance have been tested. After the oral administration of each substance, the animals have been kept under observation for a period of 10 days. No death has been noted for each of the doses administered and the animals have not manifested any toxic symptoms of any significance.

It is, therefore, concluded that the 7-acylderivatives of ursodeoxycholic acid exhibit a significant antilithiasic activity in the model of cricetidae with a diet, which induces biliary lithogenesis. The derivatives do not exhibit any substantial toxicity by acute administration in high doses, ($DL_{50}$ greater than 2,000 mg/kg), nor do they exhibit toxicity during the test for the prevention of lithogenesis, which test may be considered equivalent to a sub-acute toxicity.

The compounds of formula (I) may be administered to patients affected by biliary calculosis and biliary diskinesia in doses of 50-500 mg, administered 1-4 times daily. The manner of administration may be the same as conventionally used in pharmaceutical formulations; particularly suitable are the capsules Scherer.

The conventional inert pharmaceutically compatible excipients may be incorporated in the pharmaceutical compositions according to the present invention.

What is claimed is:

1. The compound 7-oleyl-ursodeoxycholic acid.

* * * * *